United States Patent [19]

Tolman et al.

[11] Patent Number: 4,897,479

[45] Date of Patent: Jan. 30, 1990

[54] ARYLSULFONYLOXY PURINE INTERMEDIATES

[75] Inventors: Richard L. Tolman, Warren; Wallace Ashton, Clark; Malcolm Maccoss, Freehold, all of N.J.

[73] Assignee: Merck & Co., Inc., Rahway, N.J.

[21] Appl. No.: 165,360

[22] Filed: Feb. 29, 1988

Related U.S. Application Data

[63] Continuation of Ser. No. 40,698, Apr. 20, 1987, abandoned, which is a continuation of Ser. No. 793,080, Oct. 31, 1985, abandoned, which is a continuation of Ser. No. 538,019, Sep. 30, 1983, abandoned.

[51] Int. Cl.⁴ .................. C07D 473/18; C07D 473/26; C07F 9/65; A61K 31/675
[52] U.S. Cl. .................................... 544/244; 544/276; 544/277
[58] Field of Search ....................... 544/244, 276, 277; 514/81

[56] References Cited

U.S. PATENT DOCUMENTS

| | | | |
|---|---|---|---|
| 4,027,025 | 5/1977 | Schaeffer | 544/276 X |
| 4,146,715 | 3/1979 | Schaeffer | 544/276 |
| 4,199,574 | 4/1980 | Schaeffer | 544/244 X |
| 4,287,188 | 9/1981 | Schaeffer | 544/244 X |
| 4,347,360 | 8/1982 | Ogilvie | 544/276 |
| 4,355,032 | 10/1982 | Verheyden et al. | 544/276 X |
| 4,360,522 | 11/1982 | Schaeffer | 544/244 X |
| 4,556,659 | 12/1985 | Verheyden et al. | 514/262 |
| 4,565,868 | 1/1986 | Verheyden et al. | 544/244 |
| 4,590,269 | 5/1986 | Prisbe et al. | 544/276 |
| 4,806,642 | 2/1989 | Sircar et al. | 544/244 |
| 4,816,447 | 3/1989 | Ashton et al. | 514/81 |

FOREIGN PATENT DOCUMENTS

| | | |
|---|---|---|
| 72027 | 2/1983 | European Pat. Off. |
| 74306 | 3/1983 | |
| 0085424 | 8/1983 | European Pat. Off. |

OTHER PUBLICATIONS

Steven S. Good and Paulo de Miranda; Metabolic Disposition in Rats of a Potential Prodrug of Acyclovir; Apr. 23, 1982; p. 1733, Biotransformation II.

*Primary Examiner*—Mukund J. Shah
*Assistant Examiner*—Diana G. Rivers
*Attorney, Agent, or Firm*—Richard S. Parr; Michael C. Sudol

[57] ABSTRACT

Compounds of the formula

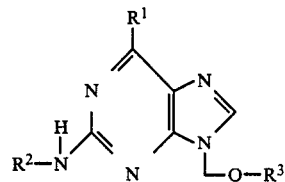

and the pharmaceutically acceptable salts thereof are disclosed. In these compounds, $R^1$ is halogen, —$SR^4$ wherein $R^4$ is H or alkyl of 1 to 4 carbon atoms, —$OCH_3$, —$OSO_2Ar$ wherein Ar is phenyl or alkyl substituted phenyl wherein the alkyl group has 1 to 6 carbon atoms, —$NR^4R^5$ wherein $R^4$ is as defined above and $R^5$ is H, alkyl of 1 to 4 carbon atoms, amino, alkanoyl of 1 to 8 carbon atoms, benzoyl, methoxy or hydroxy or $R^1$ is —$N(CH_3)_3{}^+X^-$ wherein
X is halogen or —$OSO_2Ar$ wherein Ar is phenyl or alkyl substituted phenyl wherein the alkyl group has 1 to 6 carbon atoms;
$R^2$ is H, alkanoyl of 1 to 8 carbon atoms or benzoyl;
$R^3$ is A or B wherein
A is

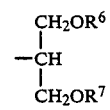

and B is

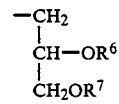

wherein $R^6$ and $R^7$ are independently selected from H and

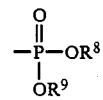

wherein $R^8$ and $R^9$ are independently selected from pharmaceutically acceptable cations and H, or $R^6$ and $R^7$ taken together are

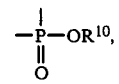

wherein $R^{10}$ is selected from pharmaceutically acceptable cations and H; with the proviso that $R^4$ is not H when: $R^5$ is H, $R^3$ is A, and $R^6$ and $R^7$ are H. The compounds have anti-viral activity.

1 Claim, No Drawings

ARYLSULFONYLOXY PURINE INTERMEDIATES

This application is a continuation of application Ser. No. 07/040,698, filed Apr. 20, 1987, which is a continuation of application Ser. No. 06/793,080, filed Oct. 31, 1985, which, in turn, is a continuation of application Ser. No. 06/538,019, filed Sept. 30, 1983, all now abandoned.

The present invention relates to purine derivatives. These compounds have anti-viral activity. The compounds are particularly effective against herpes viruses e.g., herpes simplex virus.

The present invention relates to compounds of the formula

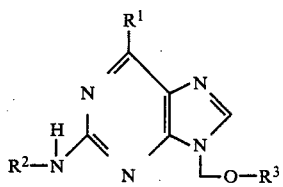

and the pharmaceutically acceptable salts thereof wherein $R^1$ is halogen (i.e. fluorine, chlorine, bromine or iodine; preferably chlorine), —$SR^4$ wherein $R^4$ is H or alkyl of 1 to 4 carbon atoms, —$OCH_3$, —$OSO_2Ar$ wherein Ar is phenyl or alkyl substituted phenyl wherein the alkyl group has 1 to 6 carbon atoms, —$NR^4R^5$ wherein $R^4$ is as defined above and $R^5$ is H, alkyl of 1 to 4 carbon atoms, amino, alkanoyl of 1 to 8 carbon atoms, benzoyl, methoxy or hydroxy, or $R^1$ is —$N(CH_3)_3{}^+X^-$ wherein X is halogen (i.e. fluorine, chlorine, bromine or iodine; preferably chlorine) or —$OSO_2Ar$ wherein Ar is as defined above;

$R^2$ is H, alkanoyl of 1 to 8 carbon atoms or benzoyl;

$R^3$ is A or B wherein

A is

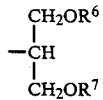

and B is

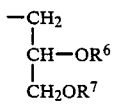

wherein $R^6$ and $R^7$ are independently selected from H and

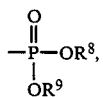

wherein $R^8$ and $R^9$ are independently selected from pharmaceutically acceptable cations (e.g. sodium, calcium, ammonium and butylammonium and preferably, sodium) and H, or $R^6$ and $R^7$ taken together are

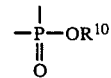

wherein $R^{10}$ is selected from pharmaceutically acceptable cations (e.g. sodium, calcium, ammonium and butylammonium and preferably, sodium) and H; with the proviso that $R^4$ is not H when: $R^5$ is H, $R^3$ is A, and $R^6$ and $R^7$ are H. Preferably, $R^1$ is —$NH_2$, —$NHCH_3$ or —SH; $R^2$ is H; and $R^6$ and $R^7$ are both H or $R^6$ and $R^7$ taken together are

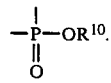

Preferred compounds of the present invention are those of the aforementioned compounds wherein $R^1$ is —$NH_2$, —$NHCH_3$ or —SH, $R^2$ is H and $R^6$ and $R^7$ are each H or $R^6$ and $R^7$ taken together are

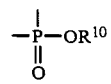

wherein $R^{10}$ is as defined above.

The present invention also relates to methods of preparing the aforementioned compounds and to the use of such compounds in treating viral infections. Compounds wherein $R^1$ is arylsulfonyloxy or trimethylammonium chloride are also particularly useful intermediates in preparing other compounds of the present invention.

The following compounds are representative of the compounds of the present invention:
9-(1,3-dihydroxy-2-propoxymethyl)-2-amino-purin-6-thione;
9-(1,3-dihydroxy-2-propoxymethyl)-2-amino-6-methylaminopurine;
9-(1,3-dihydroxy-2-propoxymethyl)-2-amino-6-ethylaminopurine;
9-(1,3-dihydroxy-2-propoxymethyl)-2-amino-6-n-propylaminopurine;
9-(1,3-dihydroxy-2-propoxymethyl)-2-amino-6-(2-propylamino)purine;
9-(1,3-dihydroxy-2-propoxymethyl)-2-amino-6-dimethylaminopurine;
9-(1,3-dihydroxy-2-propoxymethyl)-2-amino-6-hydrazinopurine;
9-(1,3-dihydroxy-2-propoxymethyl)-2-amino-6-hydroxylaminopurine;
9-(1,3-dihydroxy-2-propoxymethyl)-2-amino-6-methoxylaminopurine;
9-(1,3-dihydroxy-2-propoxymethyl)-2-amino-6-diethylaminopurine;
9-(1,3-dihydroxy-2-propoxymethyl)-2-amino-6-methoxypurine;
9-(1,3-dihydroxy-2-propoxymethyl)-2-amino-6-methylmercaptopurine;
9-(1,3-dihydroxy-2-propoxymethyl)-2-amino-6-ethylmercaptopurine;

9-(1,3-dihydroxy-2-propoxymethyl)-2-acetamido-6-(2,4,6-triisopropylbenzenesulfonyloxy)purine;
9-(1,3-dihydroxy-2-propoxymethyl)-2,6-diacetamidopurine;
9-[(1,3-dihydroxy-2-propoxymethyl)-2-acetamidopurin-6-yl]trimethylammonium chloride;
9-(2,3-dihydroxy-1-propoxymethyl)-2-amino-purin-6-thione;
9-(2,3-dihydroxy-1-propoxymethyl)-2-amino-6-methylaminopurine;
9-(2,3-dihydroxy-1-propoxymethyl)-2-amino-6-ethylaminopurine;
9-(2,3-dihydroxy-1-propoxymethyl)-2-amino-6-n-propylaminopurine;
9-(2,3-dihydroxy-1-propoxymethyl)-2-amino-6-(2-propylamino)purine;
9-(2,3-dihydroxy-1-propoxymethyl)-2-amino-6-dimethylaminopurine;
9-(2,3-dihydroxy-1-propoxymethyl)-2-amino-6-hydrazinopurine;
9-(2,3-dihydroxy-1-propoxymethyl)-2-amino-6-hydroxylaminopurine;
9-(2,3-dihydroxy-1-propoxymethyl)-2-amino-6-methoxylaminopurine;
9-(2,3-dihydroxy-1-propoxymethyl)-2-amino-6-diethylaminopurine;
9-(2,3-dihydroxy-1-propoxymethyl)-2-amino-6-methoxypurine;
9-(2,3-dihydroxy-1-propoxymethyl)-2-amino-6-methylmercaptopurine;
9-(2,3-dihydroxy-1-propoxymethyl)-2-amino-6-ethylmercaptopurine;
9-(2,3-dihydroxy-1-propoxymethyl)-2-acetamido-6-(2,4,6-triisopropylbenzenesulfonyloxy)purine;
9-(2,3-dihydroxy-1-propoxymethyl)-2,6-diacetamidopurine;
9-[(2,3-dihydroxy-1-propoxymethyl)-2-acetamidopurin-6-yl]trimethylammonium chloride;
9-(2,3-dihydroxy-1-propoxymethyl)-2,6-diaminopurine;
9-[(2-hydroxy-1,3,2-dioxaphosphorinan-5-yl)oxymethyl]-2,6-diaminopurine P-oxide;
9-[(2-hydroxy-1,3,2-dioxaphosphorinan-5-yl)oxymethyl]-2-aminopurin-6-thione P-oxide;
9-[(2-hydroxy-1,3,2-dioxaphosphorinan-5-yl)oxymethyl]-2-amino-6-chloropurine P-oxide;
9-[(2-hydroxy-1,3,2-dioxaphospholan-4-yl)methoxymethyl]-2,6-diaminopurine P-oxide;
9-[(2-hydroxy-1,3,2-dioxaphospholan-4-yl)methoxymethyl]-2-aminopurin-6-thione P-oxide;
9-[(2-hydroxy-1,3,2-dioxaphospholan-4-yl)methoxymethyl]-2-amino-6-chloropurine P-oxide.

The following compounds of the present invention are also particularly useful as intermediates for preparing compounds of the present invention:
9-(1,3-dihydroxy-2-propoxymethyl)-2-acetamido-6-(2,4,6-triisopropylbenzenesulfonyloxy)purine;
9-[(1,3-dihydroxy-2-propoxymethyl)-2-acetamidopurin-6-yl]trimethylammonium chloride;
9-(2,3-dihydroxy-1-propoxymethyl)-2-acetamido-6-(2,4,6-triisopropylbenzenesulfonyloxy)purine;
9-[(2,3-dihydroxy-1-propoxymethyl)-2-acetamidopurin-6-yl]trimethylammonium chloride.

The following are preferred compounds of the present invention:
9-(1,3-dihydroxy-2-propoxymethyl)-2-aminopurin-6-thione;
9-(1,3-dihydroxy-2-propoxymethyl)-2-amino-6-methylaminopurine;
9-(2,3-dihydroxy-1-propoxymethyl)-2-aminopurin-6-thione;
9-(2,3-dihydroxy-1-propoxymethyl)-2-amino-6-methylaminopurine;
9-(2,3-dihydroxy-1-propoxymethyl)-2,6diaminopurine;
9-[(2-hydroxy-1,3,2-dioxaphosphorinan-5-yl)oxymethyl]-2,6-diaminopurine P-oxide;
9-[(2-hydroxy-1,3,2-dioxaphosphorinan-5-yl)oxymethyl]-2-aminopurin-6-thione P-oxide;
9-[(2-hydroxy-1,3,2-dioxaphosphorinan-5-yl)oxymethyl]-2-amino-6-chloropurine P-oxide;
9-[(2-hydroxy-1,3,2-dioxaphospholan-4-yl)methoxymethyl]-2,6-diaminopurine P-oxide;
9-[(2-hydroxy-1,3,2-dioxaphospholan-4-yl)methoxymethyl]-2-aminopurin-6-thione P-oxide;
9-[(2-hydroxy-1,3,2-dioxaphospholan-4-yl)methoxymethyl]-2-amino-6-chloropurine P-oxide.

The following reaction scheme illustrates the preparation of the compounds of the present invention having side chain A:

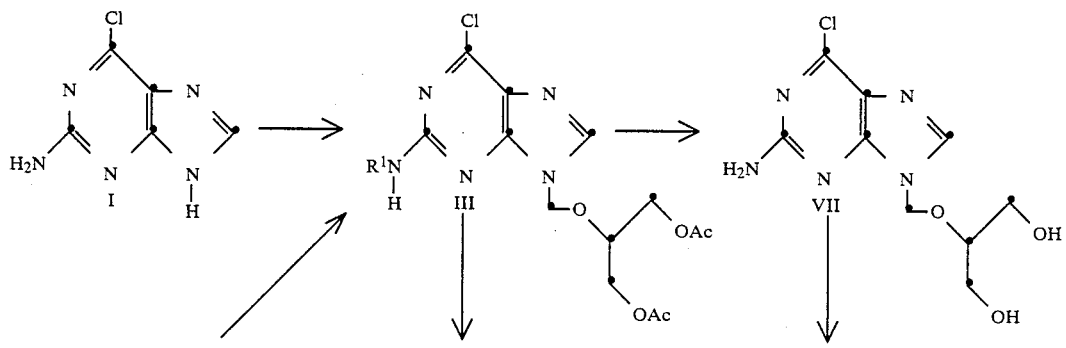

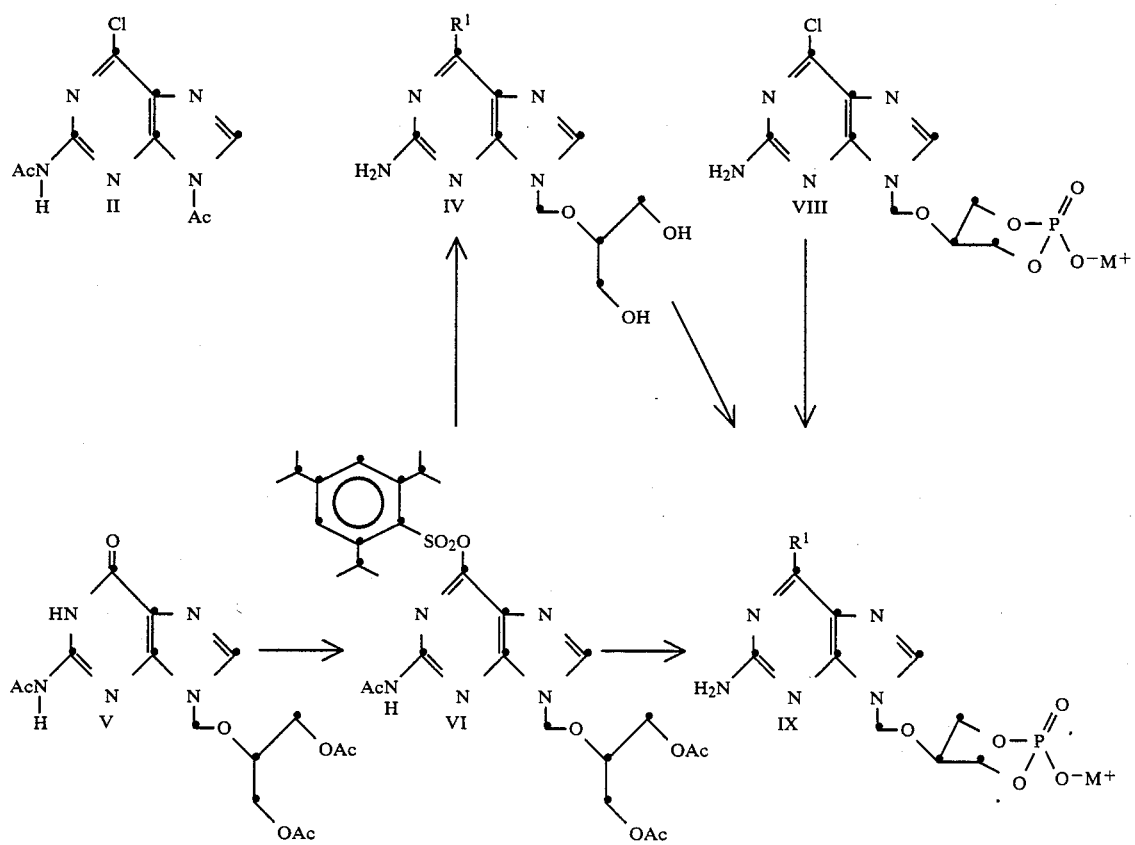

The compounds of the present invention may be prepared by reacting a 6-halo-2-aminopurine (I), or a 2-monoacylated, 9-acylated derivative thereof (II) with acetoxymethyl 1,3-diacetoxy-2-propyl ether to give a 2-amino or 2-acylamino-6-chloro-9-(1,3-diacetoxy-2-propoxymethyl)purine compound of formula III.

Reaction of a compound of formula III with hydrogen sulfide, ammonia, amines, simple alkanols, hydrazine, or hydroxylamine and removal of the acyl protecting groups gives the compound of formula IV where $R^1$ has the meaning given previously.

Alternatively, after the activation of an acylated preformed guanine acyclonucleoside V with an arylsulfonyl chloride (formula VI), the subsequent nucleophilic displacement proceeds either directly with the desired nucleophile or in some cases more efficiently after formation of another, more reactive intermediate with trimethylamine. For example, when $R_1H$ is $NH_3$, $N_2H_4$, or $CH_3OH$, the reaction more efficiently provides the desired product when a trimethylammonium intermediate is prepared. This is done by first treating the compound of formula VI with anhydrous trimethylamine followed by $R^1H$.

Deprotection of the compound of formula III gives the 6-halo compound of formula VII.

Reaction of the compound of formula IV or VII with phosphorus oxychloride in triethyl phosphate gives a cyclic phosphate compound of formula IX or VIII respectively. Reaction of the free acid of the cyclic phosphate with an alkali metal hydroxide, $NH_4OH$, substituted ammonium hydroxide, $Mg(OH)_2$, $Fe(OH)_2$ or manganese hydroxide gives the corresponding salt of the compound of formula VIII. Reacting a compound of formula VIII with $R^1H$ gives a compound of formula IX.

The cyclic phosphate derivatives can alternately be prepared by partial deprotection of the compound of formula VI with aqueous alkali hydroxide and then phosphorylation of the product by the method of conversion of a compound of formula IV to a compound of formula IX and displacement of the 6-arylsulfonyloxy group by the same method used in the conversion of compounds of formula VIII to those of formula IX.

Compounds where $R^3$ is side chain B are similarly prepared. See, for example, Examples 15 and 16.

In another aspect of the invention there is provided a pharmaceutical composition or preparation comprising a compound of the present invention together with a pharmaceutically acceptable carrier therefor. In a particular aspect the pharmaceutical composition comprises a compound of the present invention in effective unit dosage form.

As used herein the term "effective unit dosage" or "effective unit dose" is denoted to mean a predetermined antiviral amount sufficient to be effective against the viral organisms in vivo. Pharmaceutically acceptable carriers are materials useful for the purpose of administering the medicament, and may be solid, liquid or gaseous materials, which are otherwise inert and medically acceptable and are compatible with the active ingredients.

These pharmaceutical compositions may be given parenterally, orally, used as a suppository or pessary, applied topically as an ointment, cream, aerosol, powder, or given as eye or nose drops, etc., depending on whether the preparation is used to treat internal or external viral infections.

For internal infections the compositions are administered orally or parenterally at dose levels of about 0.1 to 250 mg per kg, preferably 1.0 to 50 mg per kg of mammal body weight, and are used in man in a unit dosage form, administered, e.g. a few times daily, in the amount of 1 to 250 mg per unit dose.

For oral administration, fine powders or granules may contain diluting, dispersing and/or surface active agents, and may be presented in a draught, in water or in a syrup; in capsules or sachets in the dry state or in a non-aqueous solution or suspension, wherein suspending agents may be included; in tablets, wherein binders and lubricants may be included; or in a suspension in water or a syrup. Where desirable or necessary, flavoring, preserving, suspending, thickening or emulsifying agents may be included. Tablets and granules are preferred, and these may be coated.

For parental administration or for administration as drops, as for eye infections, the compounds may be presented in aqueous solution in a concentration of from about 0.1 to 10% more preferably 0.1 to 7%, most preferably 0.2% w/v. The solution may contain antioxidants, buffers, etc.

Alternatively for infections of the eye, or other external tissues, e.g. mouth and skin, the compositions are preferably applied to the infected part of the body of the patient as a topical ointment or cream. The compounds may be presented in an ointment, for instance, with a water soluble ointment base, or in a cream, for instance with an oil in water cream base, in a concentration of from about 0.1 to 10%, preferably 0.1 to 7%, most preferably 1% w/v.

The following examples illustrate the present invention without, however, limiting the same thereto. All temperatures are expressed in degrees Celsius. UV wavelengths are reported in nm (nanometers) and extinction coefficients are in parenthesis following the indicated wavelengths.

EXAMPLE 1

N-Acetyl-2-acetamido-6-chloropurine

2-Amino-6-chloropurine (2.38 g) was heated in acetic anhydride (25 ml) at reflux. Heating was discontinued 30 minutes after solution had occurred and the yellow solution was allowed to stand at ambient temperature overnight. The crude product was filtered (2.2 g) and recrystallized from 5% aqueous methanol to furnish 1,37 g pure product (m.p. 290° with decomposition). Workup of filtrates gave another 0.5 g of less pure material; UV maximum (MeOH and 0.1N HCl): 288

Anal. Calc'd for $C_9H_8ClN_5O_2$: C, 42.62; H, 3.18; N, 27.61; Cl, 13.98; Found: C, 42.79; H, 3.08; N, 27.66; Cl, 13.72.

EXAMPLE 2

9-(1,3-Diacetoxy-2-propoxymethyl)-2-acetamido-6-chloropurine

A round-bottomed flask (10 ml) was charged with N-acetyl-2-acetamido-6-chloropurine (2.0 g, 7.9 mmoles), 1,3-diacetoxy-2-propoxymethyl acetate (2.7 g, 10.9 mmoles), and ethanesulfonic acid (63 mg). The mixture was heated in an oil bath maintained at 130° and a vacuum was applied. Thin layer chromatography showed no heterocyclic starting material after 1.5 hours and heating was discontinued. The mixture was dissolved in dichloromethane (50 ml) and filtered through Celite. The filtrate was evaporated to a residue and chromatographed on silica gel using dichloromethane/methanol (98:2) as the eluant. The product-containing fractions were combined and evaporated to give 0.75 g of pure product, m.p. 139°–140°.

EXAMPLE 3

9-(1,3-Dihydroxy-2-propoxymethyl)-2,6-diaminopurine

Method 1:

9-(1,3-Diacetoxy-2-propoxymethyl)-2-acetamido-6-chloropurine (0.72 g, 1.9 mmoles) was heated with 25 ml of liquid ammonia in a sealed vessel at 150° for 24 hours. After venting the cooled reaction mixture and allowing residual ammonia to evaporate, the yellow residue was dissolved in hot methanol and filtered.

Concentration of the solution to 3 ml induced crystallization and the product crystals were filtered, washed with methanol, and air-dried (0.36 g, 76%).

Recrystallization from methanol provided an analytically pure sample identical in all respect to material prepared by Method 2.

Method 2:

9-(1,3-Diacetoxy-2-propoxymethyl)-2-acetamido-6 (2,4,6-triisopropylbenzenesulfonyloxy)purine (0.324 g, 0.5 mmol), prepared as described in Example 9, was dissolved in sieve-dried $CH_2Cl_2$ (1.5 mL) and cooled to 0° C. To this solution was added 3 mL of $Me_3N$ (condensed at −70°) and the mixture was stirred for 30 minutes at 0° in a pressure bottle. A white precipitate formed during the reaction. Liquid $NH_3$ (condensed at −70°, 2 mL) was added to the solution (dissolution occurred) followed by an additional 2 mL after 10 minutes. The solution was stirred in the sealed bottle for 20 hours ( 8 hours at 0°, followed by slow warming to room temperature) and the bottle was then carefully opened. After venting of the volatiles a white solid remained which was dissolved in 40% aqueous $CH_3NH_2$ (10 mL) and the solution was heated under reflux (bath temperature 70°–90° C.) for 45 minutes. The solution was evaporated to dryness and the residue dissolved in 10% aqueous MeOH and applied to a Dowex 1×2(OH−) column (1.5×25.0 cms) packed in the same solvent. Elution was with 10% aqueous MeOH, followed by 15% aqueous MeOH and fractions containing the required product were pooled and evaporated to dryness to yield 108.5 mg (85.4%) of the desired product. Recrystallization from MeOH gave white crystals; m.p. 178°–179° C.

Anal. calc'd for $C_9H_{14}N_6O_3$: C, 42.51; H, 5.55; N, 33.06; Found: C, 42.16; H, 5.69; N, 32.63.

UV: ($H_2O$) λmax 279 (9,950), 254.5 (9,240); λmin 264 (7,530); 235 (5,560), (0.01N NaOH); λmax 279 (10,070), 254.5 (9,240); λmin 264 (7,600), 235 (5,560), (0.01N HCl); λmax 290 (10,150), 250.5 (11,550); λmin 268.5 (5,330), 229 (4,180). NMR (200 MHz, $d_6$ DMSO) δ: 3.20–3.70 ($m_1$ —$CH_2$—CH—$CH_2$—+HDO), 4.72 (t, J=5.5 Hz, OH), 5.55 (s, $CH_2$-base), 5.90 (s, $NH_2$), 6.81 (s, $NH_2$), 7.94 (s, H8).

EXAMPLE 4

9-(1,3-Dihydroxy-2-propoxymethyl)-2-amino-6-purinethione 9-(1,3-Diacetoxy-2-propoxymethyl)-2-acetamido-6-chloropurine (0.22 g, 0.56 mmoles) and thiourea (0.045 g, 0.59 mmoles) were suspended in absolute ethanol (15 ml) and 1 drop of formic acid was added. After reflux for 2 hours t.l.c. (thin layer chromatography) [dichloromethane/methanol (97:3) on silica gel] showed the reaction to be complete. The mixture was cooled, concentrated in vacuo, redissolved in dichloromethane and chromatographed on silica gel using the t.l.c. system described above to furnish 0.16 g of product after appropriate fractions were combined and evaporated. This material was dissolved in 40% aqueous methylamine (5 ml) and heated at reflux for 45 minutes before evaporation to a residue under reduced pressure. Recrystallization from water gave pure product, 0.08 g, m.p. 258–259.

Anal. Calc'd for $C_9H_{13}N_5O_3S.\frac{1}{8}H_2O$: C, 39.52; H, 4.88; N, 25.61; S, 11.72; Found: C, 39.93; H, 4.89; N, 25.16; S, 11.48.

EXAMPLE 5

9(1,3-Diacetoxy-2-propxymethyl)-2-amino-6-chloropurine

A. Chloromethyl 1,3-Diacetoxy-2-propyl Ether

A solution of 2.33 g (9.4 mmoles) of acetoxymethyl 1,3-diacetoxy-2-propyl ether in 22 ml of sieve-dried methylene chloride was stirred at room temperature while a slow stream of anhydrous hydrogen chloride was passed through the solution. Anhydrous conditions were maintained throughout the reaction. After two hours the reaction was judged to be complete by nuclear magnetic resonance spectroscopy. The reaction mixture was purged with nitrogen and concentrated in vacuo. The residue was taken up in a small volume of toluene and concentrated in vacuo. This was repeated twice and then the residue was pumped in vacuo to remove residual solvent. The yield of chloromethyl 1,3-diacetoxy-2-propyl ether is 1.92 g (91%).

B. 9-(1,3-Diacetoxy-2-propoxymethyl)-2-amino-6-chloropurine

A suspension of 1.44 g (8.53 mmoles) of 2-amino-6-chloropurine in 34 ml of anhydrous dimethylformamide under a nitrogen blanket was treated with 203 mg (8.53 mmoles, 340 mg of 60% dispersion in mineral oil) of sodium hydride. After twenty minutes the reaction mixture became a solution and 1.92 g (8.53 mmoles) of chloromethyl 1,3-diacetoxy-2-propyl ether in about 7 ml of anhydrous dimethylformamide was added. The reaction was monitored by t.l.c. on silica in a 90:10:1 ($CHCl_3:CH_3OH:H_2O$) system to observe disappearance of the side chain precursor. After about two hours the reaction mixture was filtered and concentrated to a cloudy oil in vacuo. The oily product had solidified upon standing and was triturated with ether. The product was isolated by filtration, washed with ether then water, again with ether, and finally dried in vacuo over $P_2O_5$ yielding 1.4 g of product. An additional 220 mg of product was obtained by filtration after the ether washes were concentrated to a small volume.

The 1.6 g of product which was shown to be a mixture of 7- and 9-isomers by t.l.c. and nmr, was purified by chromatography on a column of 80 g (19.8 cm x 3.5 cm diameter) of E. Merck Silica Gel 60 packed in 90:10:1 ($CHCl_3:CH_3OH:H_2O$). The product was put on the column and eluted with the above 90:10:1 system. Fractions amounting to 11.5 ml were collected at 4.5 minute intervals. The elution pattern was observed using ultraviolet absorption at 310 mm and the various fractions were evaluated by t.l.c. on silica using $CHCl_3:CH_3OH:H_2O$ (90:10:1). Tubes 4 through 9 were combined and concentrated to dryness yielding 781 mg of the pure 9-isomer and tubes 12 through 14 were combined and concentrated yielding 315 mg of the pure 7-isomer.

EXAMPLE 6

9-(1,3-Dihydroxy-2-propoxymethyl)-2-amino-6-chloropurine

A solution of 781 mg (2.18 mmoles) of 9-(1,3-diacetoxy-2-propoxymethyl)-2-amino-6-chloropurine in 22 ml of methanol was treated with 109 mmoles (5 mole percent) of freshly prepared sodium methoxide. Within ten minutes the stirred solution became cloudy and the product precipitated gradually in the course of forty-five minutes. The product was isolated by filtration, washed with 10 ml of water and dried in vacuo over $P_2O_5$ yielding 507 mg of pure product. A 200 MHz nmr spectrum in $d_6$ DMSO was fully in accord with the structure.

Anal Calc'd. for $C_9H_{12}N_5O_3Cl$ (273.67): C, 39.50; H, 4.42; N, 25.59; Cl, 12.95; Found: C, 40.56 40.51; H, 4.61, 4.59; N, 25.74, 25.55; Cl, 13.04, 12.86.

EXAMPLE 7

Sodium 9-(1,3-Dihydroxy-2-propoxymethyl)-2-amino-6-chloropurine Cyclic Monophosphate A suspension of 273 mg (1 mmole) of 9-(1,3-dihydroxy-2-propoxymethyl)-2-amino-6-chloropurine in 5 ml of sieve-dried triethyl phosphate was treated with 164 mg (100 ml; ca. 1.1 mmoles) of freshly distilled phosphorus oxychloride at room temperature. Within five minutes the stirred suspension had become homogeneous.

After being allowed to stand overnight the reaction mixture was poured into 20 ml of hexane and the mixture was stirred. The hexane phase was decanted, and the residue was triturated with 15 ml of anhydrous ether. The product was isolated by filtration, washed with anhydrous ether and dried in vacuo yielding a 357-mg residue. The residue was suspended in 5 ml of water and titrated to pH 7 with 1N and then 0.1N sodium hydroxide. The resulting aqueous solution was lyophilized yielding 345 mg of sodium salt. This product on high performance ion-exchange chromatography using a Whatman Partisil PXS 10/25 SAX anion exchange column and 0.05M pH 6.6 phosphate buffer elution at the rate of 1 ml/minute showed a major peak with a retention time of 4 minutes and a minor peak with a retention time of 6.5 minutes.

The product was dissolved in 3 ml of water and passed through a 30-ml column (10.5 cm×2 cm diameter) of cation exchange resin AG50W X-4 (H+ form). Eleven milliliter fractions were collected at 5-minute intervals. Elution was monitored by ultraviolet absorption at 310 nm and fractions were combined on the basis of optical density at 310 nm. The combined fractions were lyophilized yielding 127 mg of the free acid form of the product. The 200 MHz nuclear magnetic spectrum of this product in $d_6$ DMSO and in $d_6$ DMSO-$D_2O$ is fully in accord with the projected structure.

A 25-mg portion of the above product was suspended in about 3 ml of water and titrated to pH 7 with 0.1N NaOH. The filtered solution was lyophilized yielding 25.5 mg of product in the form of the sodium salt. The 200 MHz nuclear magnetic resonance spectrum of the product in D$_2$O was fully in accord with the projected structure of the cyclic monophosphate monosodium salt. A sample was dried at 75° for 2 hours for elemental analysis.

Anal. Calc'd. for C$_9$H$_{10}$N$_5$O$_5$PClNa (357.64): C, 30.23; H, 2.82; N, 19.58; P, 8.66; Cl, 9.91; Na, 6.43. Found: C, 30.70; H, 3.15; N, 19.61; P, 9.42; Cl, 10.21; Na, 6.65.

EXAMPLE 8

Sodium 9-(1,3-Dihydroxy-2-propoxymethyl)-2,6-diaminopurine Cyclic Monophosphate, Alternately Named 9-[(2-Hydroxy-1,3,2-dioxaphosphorinan-5-yl)oxymethyl]2,6-diaminopurine P-oxide, sodium salt A 72.6 mg portion (286 mmoles) of 9-(1,3-dihydroxy-2-propoxymethyl)-2,6-diaminopurine was added to a stirred solution of 25 ml (41 mg; 268 mmoles) of freshly distilled phosphorus oxychloride in 2 ml of sieve-dried triethyl phosphate, and the mixture was stirred at room temperature overnight.

The reaction mixture was filtered and the filtrate was diluted with 10 ml of ether. The product that precipitated was isolated by filtration and washed three times with ether. The product was converted to the sodium salt after addition of 3 ml of water and titration to pH 7 with 0.1 N NaOH concentration gave an 81-mg residue.

The product was purified by ion-exchange chromatography on a 10-ml column (1.5 cm×11 cm) of the cation-exchange resin AG50W-X8 (H+ form). The column was eluted successively with water, 0.1N and 0.5N NH$_4$OH successively and 4.5-ml fractions were collected at 4-minute intervals. The major fraction was eluted with 0.5N NH$_4$OH; after the appropriate fractions were combined and concentrated to dryness, the residue was taken up in 10 ml of water. Lyophilization of the resulting solution yielded a 40-mg residue that was suspended in 3 ml of water. Titration of the suspension to pH 7 with 0.1N NaOH yielded a solution that was passed through a 10 ml (1.5 cm×11 cm) column of cation-exchange resin AG50W-X8 (Na+ form). The column was eluted with water and 7-ml fractions were collected at 3-minute intervals. The pure product was found in the first (fractions 2, 3, 4) of two closely running peaks. Lyophilization of these fractions yielded 29 mg of pure sodium 9-(1,3-dihydroxy-2-propoxymethyl)-2,6-diaminopurine cyclic monophosphate. The product had a retention time of 4.8 minutes on a Whatman Partisil PXS 10/24 SAX analytical ion exchange high performance liquid chromatography column using 0.05M pH 6.6 phosphate buffer at the rate of 1 ml/minute. The 200 MHz nuclear magnetic resonance spectrum of the product in deuterium oxide is in accord with the structure and the ultraviolet absorption spectrum is characterized by the following maxima.

UV: (0.1M pH 7 phosphate buffer) λmax 255 ( 7407), 280 ( 7913); in 0.1M HCl λmax 251 ( 9233), 291 ( 8286); (0.1M NaOH) λmax 255 ( 8015), 279 ( 8556).

Anal. Calc'd for C$_9$H$_{12}$N$_6$O$_5$PNa (338.21): C, 31.96; H, 3.58; N, 24.85; P, 9.16; Na, 6.80; Found: C, 31.67; H, 3.79; N, 24.32; P, 9.47; Na, 6.83.

EXAMPLE 9

9-(1,3-Diacetoxy-2-propoxymethyl)-2-acetamido-6-(2,4,6-triisopropylbenzenesulfonyloxy)purine To a stirred suspension of 9-(1,3-diacetoxy-2-propoxymethyl)-2-acetamido-6-purinone (0.762 g, 2 mmol) and 4-dimethylaminopyridine (0.018 g, 0.15 mmol) in sieve-dried dichloromethane (30 ml), was added triethylamine (3.3 ml) followed by 2,4,6-triisopropylbenzenesulfonyl chloride (0.890 g, 2.94 mmol). Dissolution occurred after approximately 5 minutes and the solution was stirred at room temperature overnight. The reaction mixture was then evaporated to dryness and diethyl ether (20 ml) was added to the residue. After stirring at room temperature for 15 minutes the white crystalline material (presumably triethylammonium chloride) was filtered off and washed well with ether. The filtrate and washings were evaporated to dryness to yield a brown-white foam which was dissolved in a minimum volume of dichloromethane and applied to a Kieselgel 60 silica column (3×31 cm) wet-packed in CH$_2$Cl$_2$. The column was developed successively with CH$_2$Cl$_2$, 2% MeOH in CH$_2$Cl$_2$, 5% MeOH in CH$_2$Cl$_2$ and 8% MeOH in CH$_2$Cl$_2$ and fractions containing the required product were pooled and evaporated to dryness. The stiff foam so obtained (1.18 g, 1.82 mmol, 91% yield) was chromatographically pure and was readily crystallized from diethyl ether/petroleum ether (30°-60°) to give an analytically pure sample, after drying in vacuo at room temperature over phosphorus pentoxide for 4 hours. M.P. 126°-127°; NMR (200 MHz, CDCl$_3$, shifts in δ from TMS): 1.30 (d, J=7 Hz, (CH$_3$)$_2$C), 1.99 (s, CH$_3$CO x 2), 2.41 (s, CH$_3$CO), 2.95 ("quintet", J=7 Hz, >CH—), 3.98-4.32 (m, —CH$_2$—CH—CH$_2$—), 5.70 (s, —O—CH$_2$-base), 7.30 (s, =CH— x 2), 7.97 (s, —NH—), 8.10 (s, H8).

UV (MeOH): λmax 225 (25,900), 257 (11,530), 279 (12,730); λmin 253 (11,400), 266 (9,940).

Anal. calc'd. for C$_{30}$H$_{41}$N$_5$O$_9$S: C, 55.63; H, 6.38; N, 10.81; S, 4.95. Found: C, 55.64; H, 6.35; N, 10.81; S, 5.00.

EXAMPLE 10

9-(1,3-Dihydroxy-2-propoxymethyl)-2-amino-6-n-propylaminopurine 0.113 Grams (0.175 mmol) of the title compound of Example 9 was dissolved in n-propylamine (8 ml) and the solution was stirred at room temperature for 1 hour. Water (12 ml) was then added and the solution was heated under reflux (oil-bath temp. 100°-110° C.) for 45 minutes. The solution was evaporated to dryness and the residue was dissolved in a minimum amount of H$_2$O and applied to a Dowex 1×2 column (OH form; 3×30 cm.) packed in H$_2$O. The column was developed successively with H$_2$O, 10% MeOH in H$_2$O, 20% MeOH in H$_2$O, and 30% MeOH in H$_2$O. Fractions containing the required products were pooled and evaporated to dryness to give 40 mg (77% yield) of chromatographically pure product. This material was crystallized from MeOH/diethyl ether (a solution of the material was dissolved in a little MeOH and the open flask was placed in a sealed vessel containing a small amount of ether) to give 36 mg of large crystals. M.P. 123°-124°; NMR (200 MHz, d$_6$-DMSO, δ from TMS); 0.89 (t, CH$_3$, J=7Hz), 1.59 (sextet, CH$_2$—CH$_3$, J=7 Hz), 3.00-3.70 (m, CH$_2$—CH—CH$_2$, —NH—CH$_2$—, HDO, 4.67 (t, HO—, J=5 Hz), 5.48 (s, CH$_2$-base), 5.85 (s, NH$_2$), 7.23 (s, NH), 7.83 (s, H8). UV: (H$_2$O) λmax 280 (13,684), shoulder 262 (10,056), λmin 242 (6,059), (0.01N HCL) λmax 292 (11,889), 252 (11,507); λmin 270 (7,497), 234 (6,008) (0.01N NaOH) λmax 280 (13,607), shoulder 262 (10,043); λmin 242.5 (6,123).

Anal. calc'd. for $C_{12}H_{20}N_6O_3$: C, 48.64; H, 6.80; N, 28.36. Found: C, 48.65; H, 6.99; N, 28.29.

EXAMPLE 11

Preparation of
2-Amino-6-methylamino-9-(1,3-dihydroxy-2-propoxymethyl)purine

The title compound of Example 9 (1.0 g, 1.55 mmol) was dissolved in 50 ml of $CH_3NH_2$ (condensed at $-70°$ C.) and the solution was sealed in a pressure vessel and stored at room temperature overnight. The bottle was carefully opened and the $CH_3NH_2$ allowed to boil off at room temperature. To the residue was added 40% aqueous $CH_3NH_2$ (50 ml) and the solution was gently refluxed (bath temperature 70°) for 45 minutes before being evaporated to dryness to give a yellow-white solid residue. This crude product was dissolved in a little $H_2O$ and applied to a Dowex 1×2 ($OH^-$) column (3.5×36 cms) packed in $H_2O$. Elution was carried out with stepwise increments of 10% aqueous MeOH, 20% aqueous MeOH and 30% aqueous MeOH. Fractions containing the required product were pooled and evaporated to dryness to yield 0.24 g (58%) of product. Crystallization from MeOH-$Et_2O$ by diffusion gave an analytical sample. M.p. 180°–181° C.;

Analytical Calc'd for $C_{10}H_{16}N_6O_3$: C, 44.77; H, 6.01; N, 31.33; Found: C, 44.81; H, 5.97; N, 31.19.

UV: ($H_2O$) $\lambda$max 279 (13,350), 220 (21,020), shoulder 260 (10,330); $\lambda$min 240 (5,830); (0.01N NaOH) $\lambda$max 278 (13,250), shoulder 260 (10,300), $\lambda$min 239.5 (5,930); (0.01N HCl) $\lambda$max 289 (11,360), 253 (11,780), $\lambda$min 233.5 (6,040), 270.5 (8,060).

NMR (200 MHz-$d_6$ DMSO) $\delta$: 2.92 (br, s, N—$CH_3$), 3.16—3.64 (m, $CH_2$—CH—$CH_2$+HDO), 4.66 (t, OH), 5.49 (s, O-$CH_2$-Base), 5.90 (br s, $NH_2$), 7.22 (br s, NH), 7.82 (s, H8).

EXAMPLE 12

Preparation of
2-Amino-6-hydrazino-9-(1,3-dihydroxy-2-propoxymethyl)purine

The title compound of Example 9 (0.326 g, 0.504 mmol) was dissolved in sieve-dried $CH_2Cl_2$ (1.5 ml) and cooled to 0° C. in a pressure bottle. To this was added 3 ml of $Me_3N$ (condensed at $-70°$) and the solution was stirred at 0° for 45 minutes. A white precipitate formed during the reaction. 95% Hydrazine (0.3 ml) was added and stirring was continued at 0° C. for 8 hours followed by a slow rise to room temperature (16 hours total reaction). Dissolution of the precipitate occurred immediately upon addition of hydrazine, followed by reprecipitation. Addition of MeOH gave a tractable white solid which was readily filtered to give 90.8 mg (68%) of the product in 2 crops. M.p. 213°–214° (decomp.).

Analytical Calc'd for $C_9H_{15}N_7O_3$. 0.25 $H_2O$: C, 39.48; H, 5.71; N, 35.82; Found: C, 39.28; H, 6.01; N, 36.15.

UV: ($H_2O$) $\lambda$max 281 (12,070), 257.5 (9,390) $\lambda$min 264 (9,160), 241 (7,380); (0.01N NaOH) $\lambda$max 276 (5,970), 246 (6,710), $\lambda$min 264 (5,570), 238 (6,510); (0.01N HCl) $\lambda$max 289 (11,450), 253 (11,680), $\lambda$min 270 (7,540), 231 (5,320).

NMR (200 MHz, $d_6$-DMSO+$D_2O$), $\delta$: 3.16–3.71 (m, $CH_2$—CH—$CH_2$ +HDO), 5.50 (s, O—$CH_2$— Base), 7.88 (s, H8).

EXAMPLE 13

Preparation of
2-Amino-6-methoxy-9-(1,3-dihydroxy-2-propoxymethyl)purine

The title compound of Example 9 (0.311 g, 0.48 mmol) was dissolved in sieve-dried $CH_2Cl_2$ (0.5 ml) and sieve-dried MeOH (0.35 ml) and cooled to 0° C. in a pressure bottle. To this stirred solution was added 1 ml of $Me_3N$ (condensed at $-70°$) and after 15 minutes a white precipitate was apparent. Sodium methoxide (0.138 g, 2.55 mmol) and more MeOH (0.5 ml) was added to the suspension and an opalescent solution was obtained. After 2½ hours at 0°, Bio Rex 70 (Py+ form) resin was added to neutralize the reaction and was then filtered off. The filtrate was evaporated to dryness, dissolved in a little $H_2O$ and passed through a Dowex 1×2 ($AcO^-$) column (2×21 cm). The eluate was evaporated to dryness, dissolved in a small amount of $CHCl_3$-MeOH-$H_2O$ (80:20:2 by volume) and fractionated on a silica gel 60 column (1.5×37 cm) packed and eluted with the same solvent. Fractions containing the required product were pooled and evaporated to dryness to give 87.2 mg (69%) of crude product which was crystallized from MeOH-$Et_2O$ by diffusion to give 74.2 mg of slightly contaminated product. Further purification of 49.9 mg of this material on a Dowex ×2 ($OH^-$) column (1.5×30 cm) developed in $H_2O$, 10% aqueous MeOH, then 20% aqueous MeOH gave 30.5 mg of the desired product after recrystallization from MeOH-$Et_2O$. M.p. 162°–163°.

NMR (200 Mz, $d_6$-DMSO, $\delta$ from TMS): 3.20–3.63 (m, $CH_2$—CH—$CH_2$), 3.98 (s, $CH_3$), 4.62 (t, HO, J=5.5 Hz), 5.54 (s, —$CH_2$-base), 6.49 (s, $NH_2$), 8.00 (s, H8).

UV: ($H_2O$) $\lambda$max 280 (9,090), 247 (9,590), $\lambda$min 260 (5,110), 225 (4,520); (0.01N NaOH), $\lambda$max 280 (9,090), 247 (9,590), $\lambda$min 260 (5,110), 226 (4,820); (0.01N HCl), $\lambda$max 284.5 (8,720), 244 (7,630), 209 (23,890); $\lambda$min 260 (3,680), 229 (5,480), 202 (21,760).

Analytical Calc'd for $C_{10}H_{15}N_5O_4$: C, 44.61, H, 5.62, N, 26.01. Found: C, 44.10, H, 5.57, N, 25.64.

EXAMPLE 14

Preparation of
9-(2,3-Diacetoxy-1-propoxymethyl)-2-acetamido-6-(2,4,6-triisopropylbenzenesulfonyloxy)purine A. Preparation of
$N^2$-Acetyl-9-(2,3-diacetoxy-1-propoxymethyl)guanine 10.0 Grams (39.22 mmol) of R,S-9-(2,3-dihydroxy-1-propoxymethyl)guanine was suspended in acetic anhydride (530 ml) and heated at 95°–100° C. under an air condenser from 18 hours, during which time complete dissolution occurred. After cooling to room temperature for 48 hours a white precipitate was obtained which was filtered off and washed well with ether. This gave 6.42 g of chromatographically pure material suitable for the next step. The filtrate was concentrated to small volume and ether (200 ml) was added to give a white solid. This was filtered off and washed with ether to give another 5.65 g of the required material. Total yield, 12.07 g (80.8%). An analytical sample was crystallized from MeOH-ether by diffusion with 89% recovery. M.p. 176°–178° C.

Analytical Calc'd for $C_{15}H_{19}N_5O_7$: C, 47.24; H, 5.02; N, 18.37; Found: C, 47.20; H, 5.03, N, 18.19.

UV (MeOH): λmax 277 (11,660), 257 (16,120); λmin 270 (11,510), 222.5 (2,870).

NMR (d$_6$-DMSO, δ from TMS): 1.96 (s, O-CO-CH$_3$), 1.97 (s, O-CO-CH$_3$), 2.20 (s, N-CO-CH$_3$), 3.68 (d, J=5.0 Hz, CH$_2$-OAc), 3.96–4.22 (m, O-CH$_2$-CH), 5.04 (m, —CH$_2$-CH-CH$_2$), 5.51 (s, Base-CH$_2$-O), 8.18 (s, H8).

B. 9-(2,3-Diacetoxy-1-propoxymethyl)-2-acetamido-6-(2,4,6-triisopropylbenzenesulfonyloxy)-purine 5.0 Grams (13.12 mmol) of the foregoing compound and dimethylaminopyridine (0.145 g, 1.19 mmol) were suspended in sieve-dried CH$_2$Cl$_2$ (200 ml) and Et$_3$N (23 ml) was added, followed by triisopropylbenzenesulfonyl chloride (5.84 g, 19.3 mmol). Dissolution occurred after a few minutes and the solution was stirred at room temperature for 45 minutes and then was evaporated to dryness in vacuo to give a tan-colored foam. This was triturated under ether (ca. 150 ml) and the white, non UV-absorbing crystals of Et$_3$NHCl (2.07 g) were filtered off and washed well with hot Et$_2$O. The filtrate was evaporated to dryness to give a stiff foam which was dissolved in CH$_2$Cl$_2$ and applied to a 5.0×26.0 cm silica gel column (J. T. Baker 3405) which had been wet-packed in CH$_2$Cl$_2$. Development with a step gradient of CH$_2$Cl$_2$ to 5% MeOH in CH$_2$Cl$_2$, in 1% increments eluted the product. Fractions containing the required product were pooled and evaporated to a chromatographically pure stiff foam (8.09 g, 95%) which resisted crystallization. NMR (CDCl$_3$, δ from TMS): 1.30 (2 d's, J=6.7 Hz, (CH$_3$)$_2$—C), 2.04 (s, O—CO—CH$_3$), 2.06 (s, O—CO—CH$_3$), 2.42 (s, N—CO—CH$_3$), 2.96 (sept, J=6.7 Hz, —CH—(CH$_3$)$_2$), 3.73 (d, J=5.2 Hz, —CH$_2$—OAc), 4.05–4.33 (m, O—CH$_2$—CH), 5.20 (m, CH$_2$—CH—CH$_2$), 5.61 (s, O CH$_2$-Base), 7.30 (s, aromatic-H's), 7.94 (s, NH), 8.06 (s, H8). Mass spectrum (EI) is consistent with title compound.

Analytical Calc'd for C$_{30}$H$_{41}$N$_5$O$_9$S$_1$: C, 55.63, H, 6.38; N, 10.81; S, 4.95; Found: C, 55.85, H, 6.37; N, 10.72; S, 5.10.

UV (MeOH):λmax 279 (13,610), 256 (13,280), 225 (29,660); λmin 267 (11,180), 252.5 (13,260), 217 (25,690).

EXAMPLE 15

Preparation of 2-Amino-6-methylamino-9-(2,3-dihydroxy-1-propoxymethyl)purine 1.0 Gram (1.55 mmol) of 9-(2,3-diacetoxy-1-propoxymethyl)-2-acetamido-6-(2,4,6-triisopropylbenzenesulfonyloxy)purine was dissolved in 50 ml of CH$_3$NH$_2$ (condensed at −70° C.) and the solution was sealed in a pressure vessel and stored at room temperature overnight. The vessel was carefully opened and the CH$_3$NH$_2$ was allowed to boil off at room temperature. To the oily residue was added 40% aqueous CH$_3$NH$_2$ (25 ml) and the solution was gently refluxed (oil-bath temperature 85° C.) for 1 hour before being evaporated to dryness. The residue was applied as a suspension in hot H$_2$O to a Dowex 1×2 (OH$^-$) column (3.0×37.0 cm) which had been packed in H$_2$O. The column was developed successively with H$_2$O, 10% aqueous MeOH and 15% aqueous MeOH and fractions containing the product were pooled and evaporated to dryness to give a chromatographically pure white residue (0.240 g, 58%). An analytical sample was recrystallized from MeOH. M.p. 160°–161° C.

Analytical Calc'd for C$_{10}$H$_{16}$N$_6$O$_3$.H$_2$O: C, 41.95; H, 6.34; N, 29.35; Found: C, 41.91, H, 6.18; N, 29.35.

UV: (H$_2$O) λmax 278.5 (14,030), shoulder 260 (10,990); λmin 239 (6,100), (0.01N NaOH),λmax 278.5 (14,210), shoulder 260 (10,990); λmin 239 (6,120), (0.01N HCl), λmax 288 (12,020), 252 (12,490); λmin 269.5 (8,540), 233 (6,480).

NMR (d$_6$-DMSO, δ from TMS): 2.92 (s, CH$_3$), 3.22–3.62 (m, CH$_2$-CH-CH$_2$), 4.52 (t, J=5.6 Hz, —CH$_2$OH), 4.76 (d, J=5.0 Hz, —CH-OH), 5.39 (s,—CH$_2$-base), 5.93 (s, NH$_2$), 7.22 (s, NH), 7.84 (s, H8).

EXAMPLE 16

Preparation of 2,6-Diamino-9-(2,3-dihydroxy-1-propoxymethyl)purine 0.688 Gram (1.032 mmol) 9-(2,3-diacetoxy-1-propoxymethyl)-2-acetamido-6-(2,4,6-triisopropylbenzenesulfonyloxy)purine was dissolved in sieve dried CH$_2$Cl$_2$ (3 ml) in a pressure bottle. To the stirred solution at 0° C. was added Me$_3$N (6 ml, condensed at −70° C.). After 30 minutes a white precipitate was evident. To this suspension was added NH$_3$ (4 ml, condensed at −70° C.) and a clear solution was obtained immediately. An additional 5 ml of liquid NH$_3$ was added after 3 hours and the solution was then stirred at 0° C. overnight. After slowly allowing the temperature to rise to room temperature, the bottle was carefully opened and the mixture allowed to evaporate to give a white residue. This was dissolved in 40% aqueous CH$_3$NH$_2$ (25 ml) and gently refluxed (oil-bath temperature 85° C.) for 1 hour before being evaporated to dryness. The residue was dissolved in hot H$_2$O and applied to a Dowex 1×2 (OH$^-$) column (3.0×33.0 cm) which had been packed in H$_2$O. The column was developed successively with H$_2$O, 10% aqueous MeOH and 15% aqueous MeOH and fractions containing the product were pooled and evaporated to dryness to give a chromatographically pure white residue (0.160 g, 61%). An analytical sample was recrystallized from MeOH. M.p. 185°–186° C.

Analytical Calc'd for C$_9$H$_{14}$N$_6$O$_3$: C, 42.51; H, 5.55; N, 33.06. Found: C, 42.38, H, 5.58, N, 32.80.

UV: (H$_2$O) λmax 278 (9,960), 253 (9,390), 213 (25,420); λmin 263 (7,650), 234 (5,640); (0.01N NaOH) max 278 (10,080), 253 (9,390); min 263 (7,650), 234 (5,700); (0.01N HCl) λmax 289 (10,100), 249.5 (11,660); λmin 267.5 (5,340), 228 (4,330).

NMR (d$_6$-DMSO, δfrom TMS): 3.18–3.64 (m, CH$_2$-CH-CH$_2$—), 4.52 (t, CH$_2$-OH, J=5.7 Hz), 4.75 (d, —CH—H, J=4.8 Hz), 5.38 (s, —CH$_2$-base), 5.85 (s, NH$_2$), 6.73 (s, NH$_2$), 7.85 (s, H8).

EXAMPLE 17

| Oil in Water Cream Base | |
|---|---|
| 2,6-Diamino-9-(2,3-dihydroxy-1-propoxymethyl)purine | 5.0 g |
| Lanolin, Anhydrous | 20.0 g |
| Polysorbate 60 | 4.0 g |
| Sorbitan Monopalmitate | 2.0 g |
| Light Liquid Paraffin | 4.0 g |
| Propylene Glycol | 5.0 g |
| Methyl Hydroxybenzoate | 0.1 g |
| Purified Water | to 100.0 g |

EXAMPLE 18

| Water Soluble Ointment Base | |
|---|---|
| 2,6-Diamino-9-(2,3-dihydroxy-1-propoxymethyl)purine | 0.5 g |
| Glycerol | 15.0 g |
| Macrogol 300 | 20.0 g |

-continued

| Water Soluble Ointment Base | |
|---|---|
| Polyethylene Glycol 1500 | 64.5 g |

EXAMPLE 19

| Tablet - (Total weight 359 mg) | |
|---|---|
| 2,6-Diamino-9-(2,3-dihydroxy-1-propoxymethyl)purine | 100 mg |
| Lactose | 200 mg |
| Starch | 50 mg |
| Polyvinylpyrrolidone | 5 mg |
| Magnesium Stearate | 4 mg |

In each of Examples 17-19, combine the listed ingredients by standard techniques.

What is claimed is:

1. A compound of the formula:

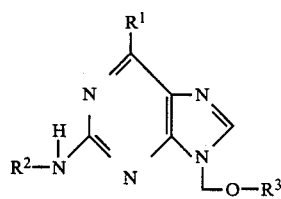

and the pharmaceutically acceptable salts thereof, wherein $R^1$ is $-OSO_2Ar$, where Ar is phenyl or alkyl-substituted phenyl, wherein the alkyl group has 1-to-6 carbon atoms: $R^2$ is H or alkanoyl of 1-to-8 carbon atoms or benzoyl: $R^3$ is A or B. wherein A is

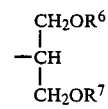

and B is

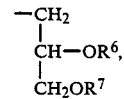

where $R^6$ and $R^7$ are independently selected from H and

wherein $R^8$ and $R^9$ are independently selected from pharmaceutically-acceptable cations and H, or $R^6$ and $R^7$ taken together are:

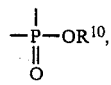

where $R^{10}$ is selected from pharmaceutically-acceptable cations and H.

* * * * *